(12) United States Patent
Tiwari

(10) Patent No.: US 9,656,304 B2
(45) Date of Patent: May 23, 2017

(54) WASHER DEVICE FOR BREAST PUMP ACCESSORIES

(71) Applicant: Anchal Tiwari, San Jose, CA (US)

(72) Inventor: Anchal Tiwari, San Jose, CA (US)

(*) Notice: Subject to any disclaimer, the term of this patent is extended or adjusted under 35 U.S.C. 154(b) by 0 days.

(21) Appl. No.: 14/675,939

(22) Filed: Apr. 1, 2015

(65) Prior Publication Data
US 2015/0352605 A1    Dec. 10, 2015

Related U.S. Application Data

(60) Provisional application No. 62/009,233, filed on Jun. 8, 2014.

(51) Int. Cl.
| | | |
|---|---|---|
| *A47L 15/00* | (2006.01) | |
| *B08B 3/10* | (2006.01) | |
| *A61M 1/06* | (2006.01) | |
| *A61L 2/02* | (2006.01) | |
| *A61L 2/00* | (2006.01) | |
| *A61L 9/00* | (2006.01) | |

(52) U.S. Cl.
CPC .............. B08B 3/10 (2013.01); *A47L 15/00* (2013.01); *A61L 2/00* (2013.01); *A61L 2/02* (2013.01); *A61L 9/00* (2013.01); *A61M 1/06* (2013.01); *A61M 2209/10* (2013.01)

(58) Field of Classification Search
CPC ........ A47L 15/00; A47L 15/50; A47L 15/502; A47L 15/503; A47L 15/505
See application file for complete search history.

(56) References Cited

U.S. PATENT DOCUMENTS

| | | | |
|---|---|---|---|
| 2,016,880 A | 10/1935 | Ward | |
| 2,977,963 A | 4/1961 | Klint | |
| 4,589,556 A | 5/1986 | Peretz | |
| 4,820,351 A | 4/1989 | Hambleton et al. | |
| 4,974,806 A * | 12/1990 | Matern | A47L 15/505 211/41.9 |
| 5,010,660 A | 4/1991 | Hambleton et al. | |
| 5,522,410 A * | 6/1996 | Meilleur | A47L 15/0065 134/108 |

(Continued)

OTHER PUBLICATIONS

GE Pressroom Release, let-me-count-the-waves:-new-ge-dishwasher-has-102-cleaning-jets-to-thoroughly-clean-your-dishes, Dishwasher, Oct. 9, 2013, 7 pages, GE pressroom, US.

*Primary Examiner* — David Cormier
(74) *Attorney, Agent, or Firm* — IDP Patent Services; Olav M. Underdal

(57) ABSTRACT

A washing device for washing breast pump accessories and baby bottles, by spraying water in jets of high pressure, includes a washing enclosure; a water inlet; a drain outlet; a tube network; a wash pump; a heating element; a tray; a top sliding mesh lid; a breast shield clamp, including a clip, a clamp base, and extender arm, and adjustable side arms; a distribution valve; a plurality of water dispensing components, including spray pipes, a top spinner, a bottom spinner, side spinners, side nozzles. Spray pipes can be height adjustable, and can include spray nozzles, which can be flexible or rotating. Side nozzles can be adjustable or rotating. The washing device can further include a steam generator or an ultraviolet sterilizer lamp for sterilizing contents placed in the tray.

18 Claims, 7 Drawing Sheets

(56) References Cited

U.S. PATENT DOCUMENTS

| | | |
|---|---|---|
| 6,364,131 B1 * | 4/2002 | Moylan ................. A47L 15/505 |
| | | 211/41.8 |
| 6,405,398 B1 | 6/2002 | Seidel |
| 7,165,562 B2 | 1/2007 | Myong |
| 7,318,555 B1 | 1/2008 | Ueda et al. |
| 7,914,625 B2 | 3/2011 | Bertsch et al. |
| 8,007,478 B2 | 8/2011 | Lu |
| 2003/0168087 A1 | 9/2003 | Inui et al. |
| 2004/0084068 A1 * | 5/2004 | Hur ..................... A47L 15/4255 |
| | | 134/58 D |
| 2006/0042656 A1 | 3/2006 | Welch |
| 2006/0065666 A1 | 3/2006 | Dunn et al. |
| 2006/0237044 A1 * | 10/2006 | Ferguson ............ A47L 15/0049 |
| | | 134/34 |
| 2007/0235063 A1 | 10/2007 | Lee et al. |
| 2008/0271765 A1 | 11/2008 | Burrows |
| 2009/0301530 A1 | 12/2009 | Shin et al. |
| 2012/0285491 A1 | 11/2012 | Blanchard et al. |
| 2012/0291827 A1 * | 11/2012 | Buddharaju ........ A47L 15/4278 |
| | | 134/198 |
| 2014/0263302 A1 | 9/2014 | Pipp |
| 2015/0272421 A1 * | 10/2015 | Benedict ............ A47L 15/4282 |
| | | 134/174 |

* cited by examiner

Breast Pump Accessory Washer

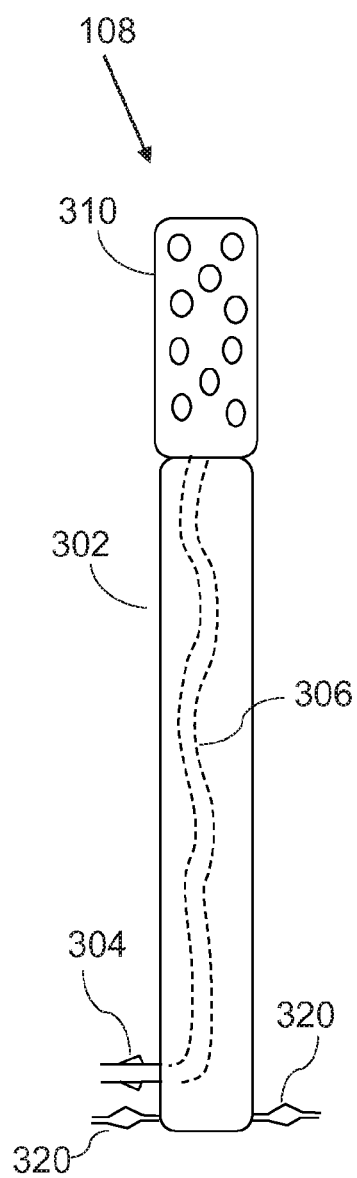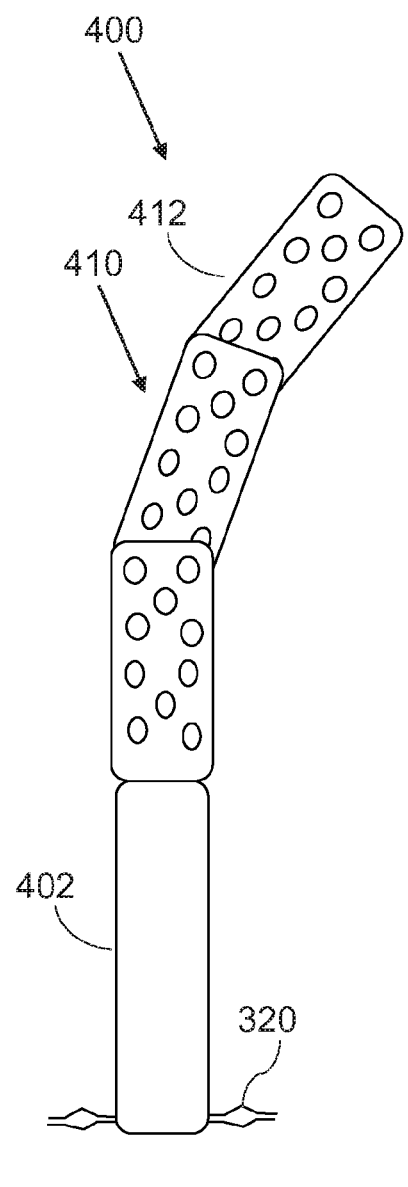
FIG. 3
FIG. 4

WASHER DEVICE FOR BREAST PUMP ACCESSORIES

CROSS-REFERENCE TO RELATED APPLICATIONS

This application claims benefit of U.S. Provisional Application No. 62/009,233 filed Jun. 8, 2014.

FIELD OF THE INVENTION

The present invention relates generally to the field of washing devices, and more particularly to devices and methods of washing and sterilizing breast pump accessories and baby bottles.

BACKGROUND OF THE INVENTION

With so many new mothers in the work field today, the need to pump breast milk while away from the home has become more and more prevalent. Many new mothers who for different reasons are not able to breast feed their babies but still want their babies to get the benefits of breast milk have to use a breast pump at home or at work.

Ensuring the proper cleaning of the breast pump and accessories can be very tedious and inconvenient with existing devices. Having access to a method of cleaning the breast pump and accessories with portability, speed and efficiency would relieve the worry of having to find a hygienic way to clean these items after use.

To maintain good hygiene it is required to wash the pump accessories and bottles after every use. Washing all these parts several times a day could be very time consuming and tiring and damaging to the hands, it can be especially challenging to do at work. Hence, the need for an automated breast pump accessories washer.

There exists on the market general dish washers and table top dishwashers, but they are not well adapted for use in cleaning breast pump accessories, and do not have special disinfecting or sterilization features. Industrial washers are available at very high-cost and may have satisfactory sterilization capabilities, but such devices are designed for washing of laboratory bottles or other industrial equipment, and generally do not have design features to accommodate cleaning of breast pump accessories.

As such, considering the foregoing, it may be appreciated that there continues to be a need for novel and improved devices and methods for cleaning breast pump accessories

SUMMARY OF THE INVENTION

The foregoing needs are met, to a great extent, by the present invention, wherein in aspects of this invention, enhancements are provided to the existing model of devices for washing and sterilizing breast pump accessories and baby bottles.

In an aspect, the breast pump accessory washer includes a running water supply, a drain, and a power supply, and can easily be used when a sink/wash basin and a nearby power supply is available. The breast pump accessory washer can be portable and can easily be installed, by attaching an inlet nozzle to a faucet, connecting a power cord to a power outlet, dropping a drain pipe in a sink, and using the washer when needed.

In a related aspect, the breast pump accessory washer uses less power and water than the dishwasher and hence can be run several times a day without having to run the whole dishwasher to clean some bottles or to clean the baby bottles along with dirty dishes.

In another related aspect, a conventional domestic dishwasher sprays water only from the bottom, which can topple the breast pump accessories and does not allow for the water jet to reach inside the breast flanges and therefore does not clean the breast pump accessories well. This device washes the breast pump accessories more effectively in less time, and also allows sterilizing them with ease.

In yet a related aspect, the simple design of the breast pump accessory washer ensures that it can be manufactured at a low cost. Even when the washer is no longer needed for cleaning breast pump accessories, mothers can use this device to wash baby bottles and sippy cups, with the option of not using the sterilizing function.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 3 is a side view of a spray pipe, according to an embodiment of the invention.

FIG. 4 is a side view of a spray pipe, according to an embodiment of the invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

Figure 1:
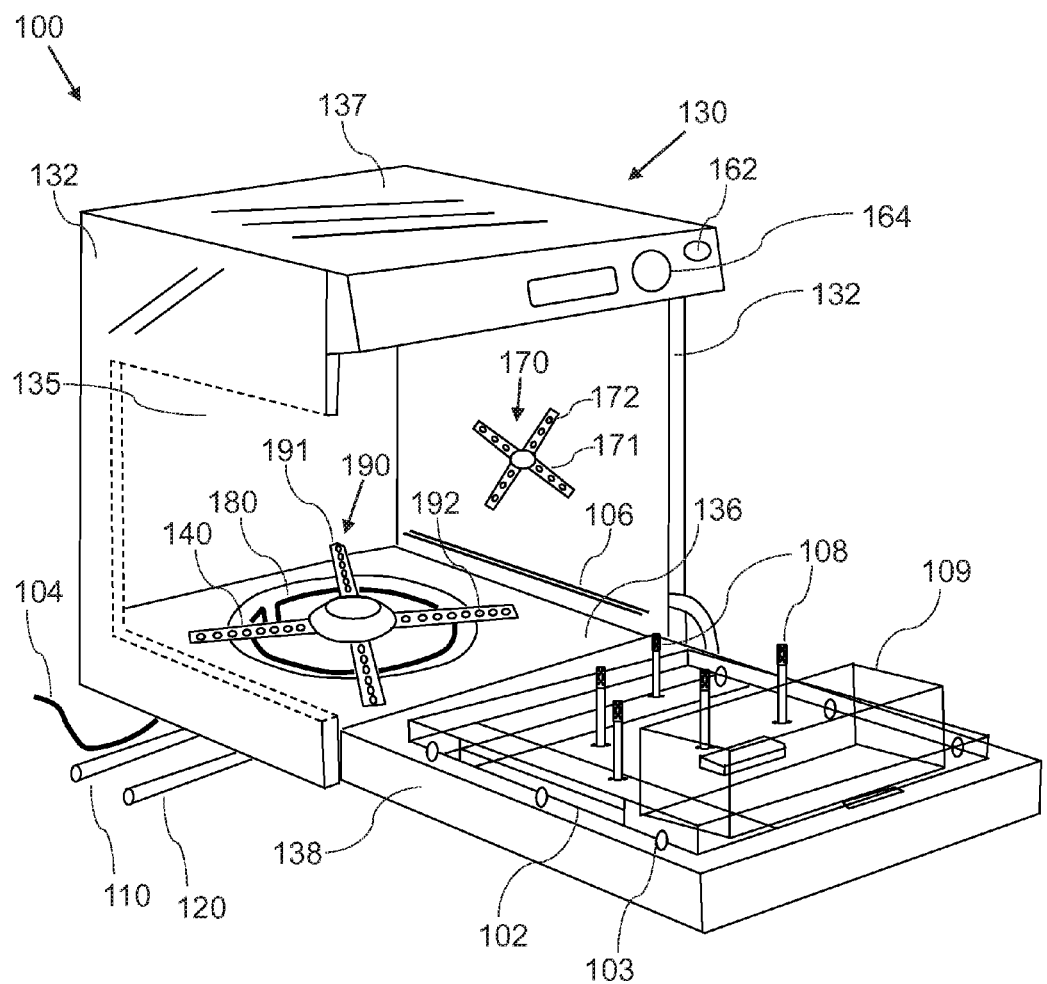
FIG. 1 is a perspective view of a breast pump accessory washer, according to an embodiment of the invention.

In the following, we describe the structure of an embodiment of a breast pump accessory washer 100, with reference to FIG. 1, in such manner that like reference numerals refer to like components throughout; a convention that we shall employ for the remainder of this specification.

In an embodiment, the breast pump accessory washer 100 can be front loading, and include:
  a. a washing enclosure 130, including side walls 132, a rear wall 135, a base section 136, a top section 137, and a hinged front door 138. The washing enclosure is here shown with a partial cut-out of one side wall 132, to show the interior of the washing enclosure 130;
  b. a mesh tray 102, which can be rolled out, and which can house breast pump accessories, which can include bottles, breast flange connectors, and other accessories. The mesh tray 102 is here shown rolled out and resting on an inner side of the opened hinged front door 138;
  c. An electric power cord 104, which can be plugged to a power supply outlet;
  d. A water inlet 110, which can include a nozzle, that can be easily screwed to a faucet of a sink or wash basin. The nozzle can be designed to fit faucets of various shapes and width and can be easily screwed to make it tight;
  e. A drain outlet 120, for draining washing water out of the breast pump accessory washer 100.

In a related embodiment, water from the inlet 110 collects in a water basin 140, also called a tub or sump 140, in an inner bottom of the washer 100, and the used water can be drained out of the washer 100, through the drain outlet 120, which can further include a drainage vent, such that the drain outlet 120 can drain water into a sink. If the washer 100 is mounted on the wall, the water inlet 110 can be connected to the water supply and the drain outlet 120 can be connected to a drainage system.

In a related embodiment, the washer 100 includes a base section 136, which can be rectangular, and can further include a water basin 140, which can be substantially circular, located in a center bottom of the base section 136.

In a related embodiment, a heating element 180 can be positioned in a center of the water basin 140, such that the heating element 180 heats the water for washing and sterilizing.

In a related embodiment, a bottom spinner or rotating wash arm 190 is mounted at the bottom inner side of the washer 100, extending from the water basin 140.

Figure 5:
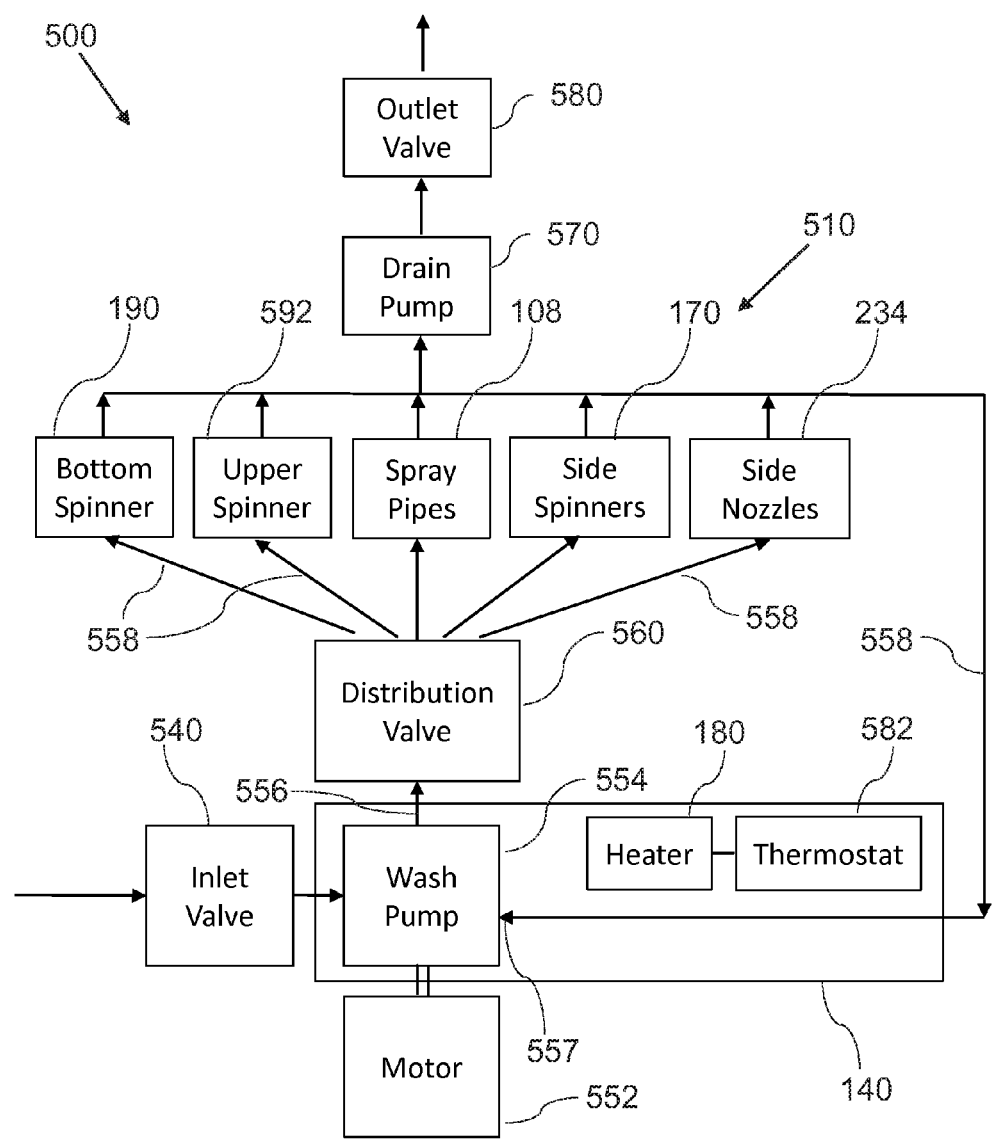
FIG. 5 is a schematic diagram illustrating fluid connectivity in a breast pump accessory washer, according to an embodiment of the invention.

In a related embodiment, as shown in FIG. 5, a wash pump 554, which can be an impeller pump, is housed in the water basin 140. It is connected or includes a motor 552, which sits right below the tub 140.

In a related embodiment, each of two sidewalls 132 to the right and left side can have vertically oriented side spinners 170 connected on inner sides of the sidewalls 132, such that the side spinners 170 spray heated water mixed with detergent on the contents in the tray from the right and left sides.

In an embodiment, an upper spinner 592 can be positioned in a top part of the inside of the washer, to spray washing water from the top, inside the washing enclosure 130.

In a related embodiment, a mesh tray 102 can sit over rails 106 in the sidewalls right over the spinner inlay without touching it. The tray 102 can include rollers 103, or alternatively drawer slides, on each side, such that the rollers 103 allow the tray to be rolled/pulled in or out over guide rails 106 on the inner side walls of the washer. FIG. 1 shows the tray 102 in a rolled out configuration, wherein the tray 102 is resting on an inner side of the open washer door 138.

In a further related embodiment, the tray 102 can include vertical spray pipes 108 on which breast shield connectors and bottles can be placed in an inverted orientation.

Figure 7:
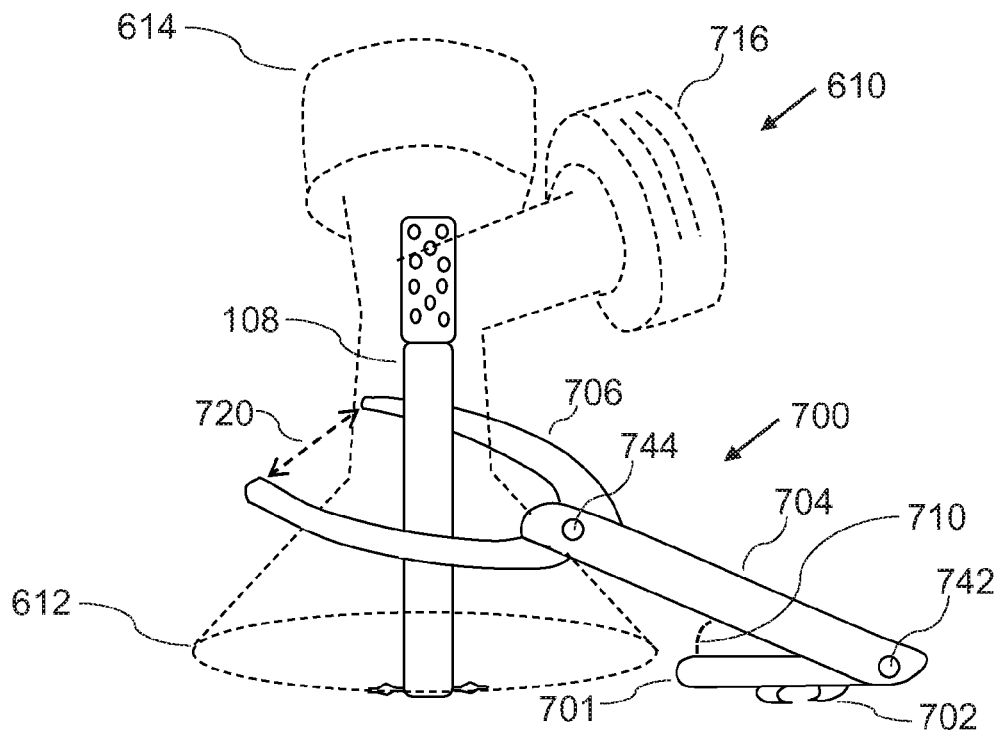
FIG. 7 is a perspective view of a spray pipe with a mounted breast flange connector held in place by a breast shield clamp, according to an embodiment of the invention.

As shown in FIG. 7, a breast flange connector 610, sometimes called a breast shield connector, here shown in dotted lines, is a well-known device which attaches to a breast pump, to aid in pumping milk from a breast into a bottle 620, which typically can include:
  a. A breast flange 612, which is placed on the breast, and acts as a funnel;
  b. A pump connector 614, which is connected to a breast pump, such that there is a fluid connection, such as a tunnel or tube connection, between the opening of the breast flange 612 and the opening of the pump connector 614;
  c. A bottle connector 716, which is in fluid connection with the tunnel between the breast flange 612 and the pump connector 614, such that a bottle 620 can be attached to the bottle connector 716, whereby milk from the breast will flow into the bottle 620, when the breast pump is operated.

In a yet further related embodiment, the spray pipes 108 spray the inside of bottles and breast flange connectors with strong jets of washing water.

In a related embodiment, as shown in FIG. 3, a spray tube 108, can further include:
  a. an elongated tube 302;
  b. a spray nozzle 310, which is connected to an upper end of the elongated tube 302;
  c. a water connector 304, which connects to the tube network 558, as shown on FIG. 5, and is in fluid with the spray nozzle 310, for example via an internal tube 306, such that washing water from the tube network 558 can spray from the spray nozzle 310;
  d. at least one clip 320, which is connected to a lower end of the elongated tube 302, and is configured to clip on to the mesh tray 102, such that the spray tube 108 is connected to the mesh tray 102.

Figure 2:
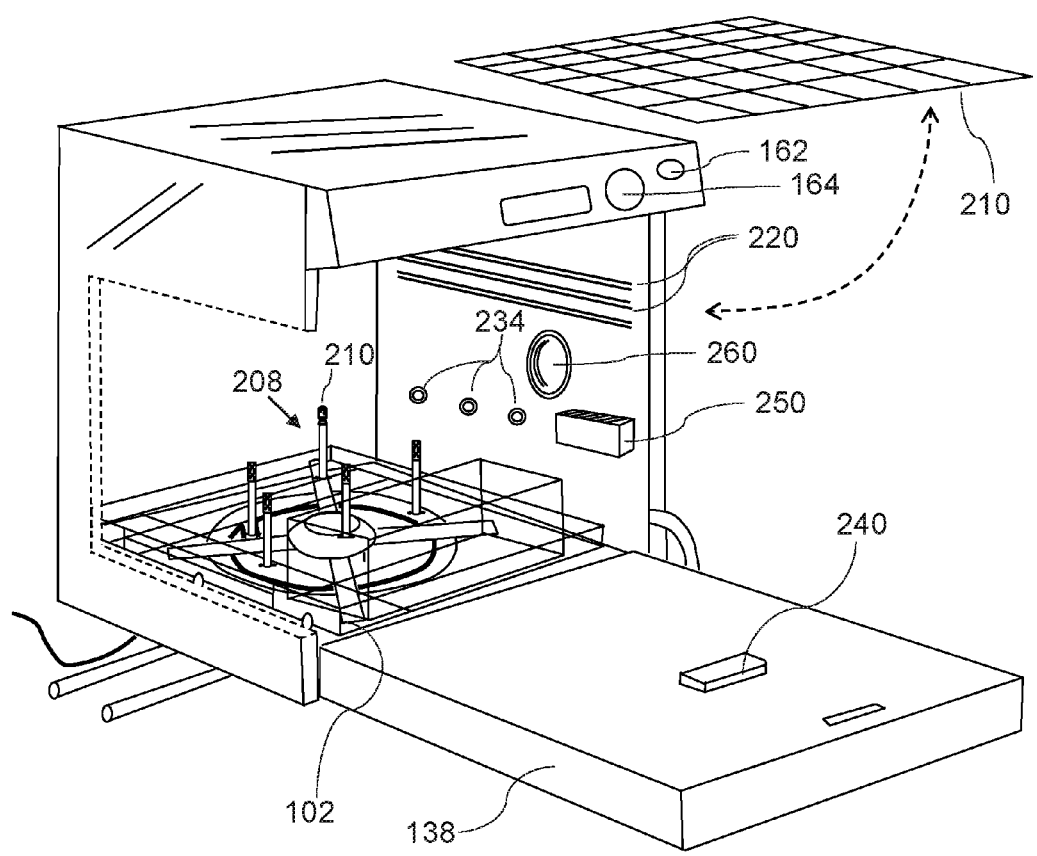
FIG. 2 is a perspective view of a breast pump accessory washer, according to an embodiment of the invention.

In a related embodiment, as shown in FIG. 2, a spray pipe 208 can be configured with a spray nozzle 310 that is configured as a rotating spray nozzle 210. A rotating spray nozzle 210 can be manufactured according to well-known designs for nozzles that self-rotate when they emit liquid under pressure, such as for example Typhoon™ self-rotating nozzles manufactured by NLB Corp.

In a related embodiment, as shown in FIG. 4, the spray nozzle 310, can be configured as a flexible elongated spray nozzle 410, for example of the goose neck type, comprising pivotally connected segments 412, such that the shape of the flexible elongated spray nozzle 410 can be adjusted.

Figure 6:
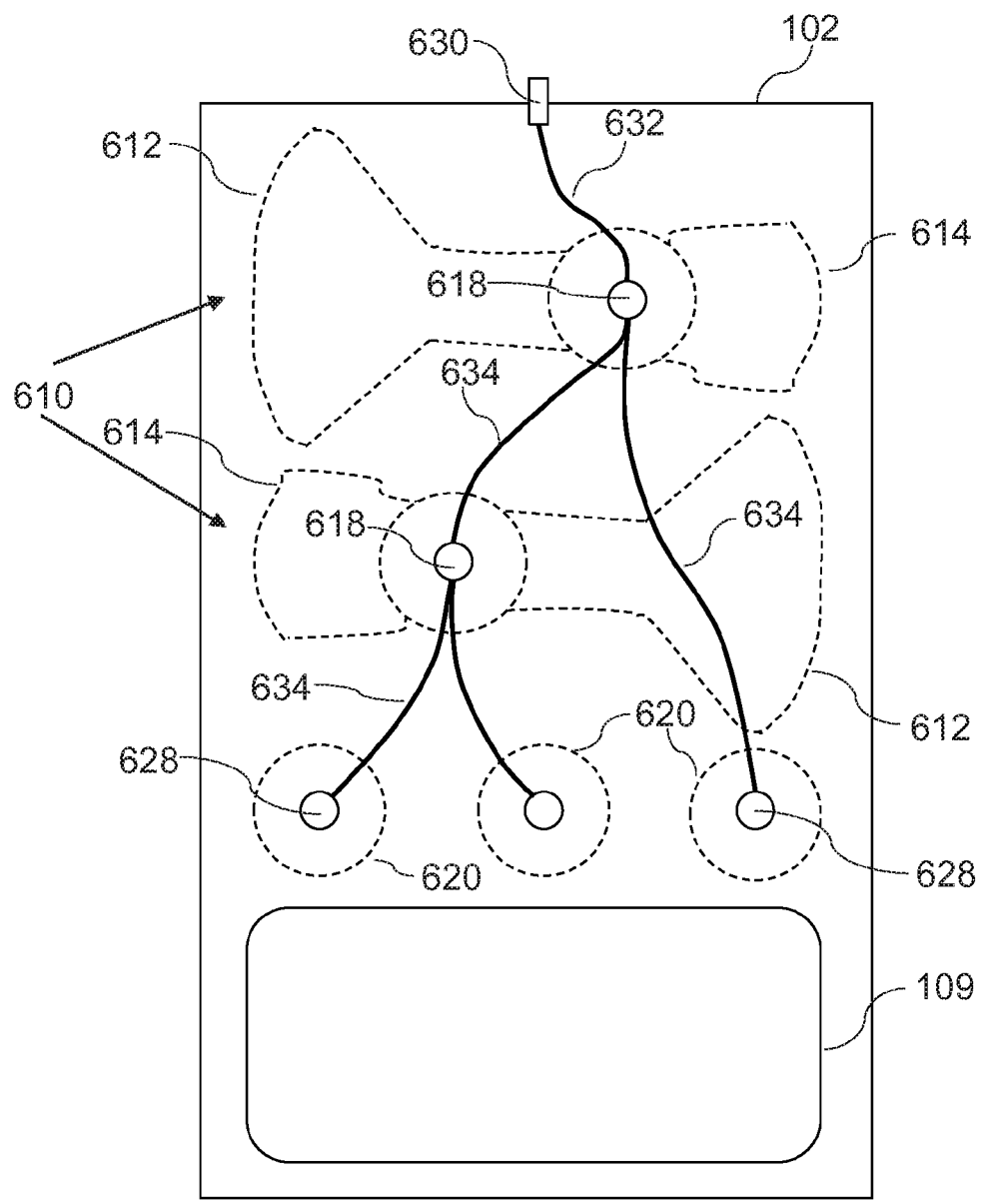
FIG. 6 is a top view of a tray with installed spray pipes, according to an embodiment of the invention.

In a related embodiment, as shown in FIG. 6, flange spray pipes 628 can be placed in a configuration, so as to allow spacing for a wide opening 612, or breast flange 612, and a narrow opening 614, or pump connector 614, of two breast flange connectors 610 such the openings are right in front of side spinners 170 on the side walls 132, whereby the breast flange connectors 610 are cleaned well by the water sprayed from the side spinners 170 on the side walls 132. FIG. 6 further shows bottles 620 mounted on bottle spray pipes 628.

In a related embodiment, the spray pipes 108 can be attached with tray tubes 634 that branch out from a main tray tube 632 connected to a tray inlet nozzle 630 at the back of the tray, which connect to a washer tube network 558, as shown on FIG. 5, which provides washing water under high pressure to the spray pipes 618 628. When the tray is rolled all the way back, the inlet nozzle 630 is latched on to the washer tube network 558, as shown in FIG. 5, which feeds washing liquid to a tube connector on the inner back wall of the washer 100.

In a further related embodiment, the spray pipes 618 for the breast flange connectors 610 can be shorter than the spray pipes 628 for the bottles in order to allow the breast flange connectors 610 to sit snuggly in to the tray.

In a related embodiment, a removable mesh basket 109, which can be made from metal, plastic, or a composite, and can further include a hinged lid, which can be fitted in the tray 102. The basket 109 can hold nipple protectors, rings, silicon valves and other smaller accessories of the breast pump. These smaller parts can just be dropped into this box, after which the hinged lid can be closed.

In a related embodiment, as shown in FIG. 5, a drain pump 570 can be connected with the motor 552, or alternatively can be driven by a separate drain motor. The drain pump 570 drains dirty washing water through the drain outlet in to a drain pipe, which drains in to the sink or drainage system.

In a related embodiment, as shown in FIG. 2, a top sliding mesh lid 210 slides and snaps in to grooves 220 on the side walls on top inner sides of the washer 100, to secure the bottles and breast flange connectors 610 that are positioned in the mesh tray 102. The top sliding mesh lid 210 can be adjusted to three different heights based on the height of the bottles that need to be washed. The top sliding mesh lid 210 can be made of a mesh material to allow the water to circulate freely in the top part of the inside of the washer 100. The top sliding mesh lid 210 keeps the bottles and breast flange connectors 610 from toppling and holds them in place for effective cleaning from inside.

In a related embodiment, as shown in FIG. 2, a detergent dispenser 240 can be located on an inside of the door 138. Alternatively, the detergent dispenser 240 can further be placed at the front of the unit and can be filled by pulling out the tray in the front when the unit is closed). During the wash cycle the washing liquid or powder content of the detergent dispenser is released in the tub 140, where it is mixed with the washing water. FIG. 2 shows the mesh tray 102 in a rolled in configuration, such that is inside the washing enclosure 130, resting on the base section 136.

In a related embodiment, a power switch 162 can turn the power on, and a control knob 164 can indicate wash cycles, which can for example include a quick cycle of 15 minutes duration and a long cycle of 25 minutes duration, or another number of predetermined cycles of a predetermined length. The short cycle can for example have a rinse and wash cycle, followed by three rinse cycles. The long cycle can for example have a short cycle followed by sterilization and dry cycles. There can also be a control button for a steam cycle to sterilize the prewashed accessories and bottles.

In a related embodiment, water from the water inlet 110 gets collected at the bottom of the apparatus through an inlet valve 540. The contents from the detergent dispenser 240 can be released into the washing water at any time during the wash.

In a related embodiment, as shown in FIG. 5, depicting an overall schematic diagram of the flow of washing water 500, and fluid connectivity of the washer 100, an output tube 556 extends from the wash pump 554 and feeds in to the bottom spinner 190, upper spinner 592, spray pipes 108, side spinners 170, side nozzles 234, and any other wash water dispensing components 510, which are all connected in a fluid connection via a washer tube network 558, such that the wash pump 554 is configured to pump water in the tube network 558, such that the water circulates in the tube network 558, such that washing water flows from the wash pump 554, is dispensed from the water dispensing components 510, and then flows back to the sump 140, and then the wash pump 554.

In a related embodiment, the heating element 180 in the water basin 140 can heat the water periodically, and can further be controlled by a thermostat.

In a related embodiment, during a wash cycle the wash pump 554 draws wash liquid from the tub 140 through a pump inlet 557 and pumps the pressurized wash liquid through the pump outlet 556 to the lower wash arm, the two wash arms on the side walls and to the pump feeding in to the jets in the tray, and any other attached water delivery devices.

In a further related embodiment, a distribution valve 560 can be configured at the pump outlet 556, to selectively pump wash liquid to any component or set of components, in the wash water dispensing components 510.

In a related embodiment, the bottom spinner 190 can have two, three, four, or a plurality of blades 191, and each blade 191 can have a plurality of holes 192, which allow jets of washing water to be sprayed on the contents of the unit from the bottom. The holes 192 can be angled such that the liquid jets cause the bottom spinner 190 to spin, and the spinning motion allows for the washing liquid to be sprayed on outer and inner sides of the bottles and breast flange connectors 610, and in the basket 109 that holds smaller parts.

In a related embodiment, the upper spinner 592 can have two, three, four, or a plurality of blades, and each blade can have a plurality of holes, which allow jets of washing water to be sprayed on the contents of the washer from the top. The holes can be angled such that the liquid jets cause the upper spinner 592 to spin, and the spinning motion allows for the washing liquid to be sprayed on outer and inner sides of the bottles 620 and breast flange connectors 610, and in the basket 109 that holds smaller parts.

In a related embodiment, a side spinner 170 can comprise two, three, four, or a plurality of blades 171, and each blade 171 can have a plurality of holes 172, which allow jets of washing water to be sprayed on the contents of the washer from the side. The holes 172 can be angled such that the liquid jets cause the side spinner 170 to spin, and the spinning motion allows for the washing liquid to be sprayed on outer and inner sides of the bottles and breast flange connectors 610, and in the basket 109 that holds smaller parts.

In a related embodiment, as shown in FIG. 2, a side nozzle 234 can be mounted on an inner side wall of the washer 100, such that the side nozzle 234 is connected to the tube network, and configured to spray washing water on the contents of the tray 102.

In a further related embodiment, a plurality of rotating or spinning side nozzles 234 can be mounted on the left and right inner side walls of the washer 100, such that the rotating side nozzles 234 are configured to spray washing water on the contents of the tray 102. A rotating nozzle can be manufactured according to well-known designs for nozzles that self-rotate when they emit liquid under pressure, such as for example Typhoon™ self-rotating nozzles manufactured by NLB Corp.

In a further related embodiment, a plurality of adjustable side nozzles 234 can be mounted on the left and right side walls of the washer 100, to spray washing water on the contents of the tray 102, such that the adjustable side nozzles 234 can be manually adjusted to spray in a pre-determined direction.

In various embodiments, water spray from jets from left and right side walls of the washer 100 can ensure washing of breast flange connectors 610 from inside.

In various embodiments, during successive wash cycles, the pump at the base of the tray pressurizes the washing liquid and pumps it to the jets in the tray. High pressure jets of the wash liquid cleanse the bottles and breast flange connectors 610 from inside.

In various embodiments, distribution valve 560, or a plurality of valves, can selectively activate and deactivate water spray devices, including upper and lower wash spinner, side nozzles, side spinners, and pipe nozzles in order to direct wash liquid alternately among the water spray devices. The washing water sprayed on the contents of the tray 102, is collected into the water basin 140 and pumped back into the water spray devices that are all connected with the pump via a tube network 558. The dirty water is directed into the drain pump 570 and pumped out through the outlet valve 580 into the drain outlet 120.

In an embodiment, if a sterilization cycle is chosen, after the final rinse the inlet valve lets a small quantity of water in to the tub. The heating element heats up the water to generate steam, which sterilizes the contents. After a pre-determined interval, which allows the contents of the dishwasher to be sterilized, the vent at the top of the door allows the steam to escape which dries the bottles and accessories. In order to protect the breast pump accessory washer 100 from heat damage during a sterilization cycle, the water basin 140 can for example be manufactured in stainless steel.

Figure 9:
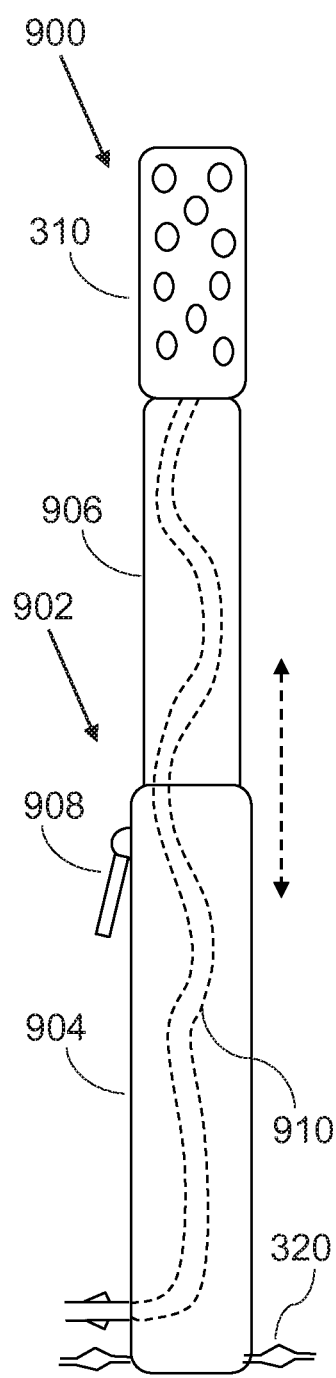
FIG. 9 is a side view of a spray pipe, according to an embodiment of the invention.

In an embodiment, as illustrated in FIG. 9, a spray pipe 108, can be configured as a length adjustable spray pipe 900, to allow length adjustment, such that the height of the spray pipe 900 can be adjustable to fit to different types of breast flange connectors 610 or bottles 620, such that the spray pipe height can be locked in place with a lever 908 or a screw type action. The length adjustable feature can include an inner or outer upper pipe 906, sliding into or over respectively an outer or inner lower pipe 904, and can be made according to well-known design principles for sealed adjustable length pipes, such as for example used in adjustable length sprinkler system nozzles. Such a construction can for example include a sealing between the lower and upper pipes 904 906, or use of an internal tube, which folds and extends inside the length adjustable spray pipe 900, as the spray pipe 900 is retracted or extended. The length adjustable spray pipe 900 can have a tube connection, at a lower end of the spray pipe 900 for connecting the spray pipe 900 with the tube network 558.

In an embodiment, as shown in FIG. 7, a breast shield clamp 700, can include:
a. a clamp base 701;
b. a clip 702, which is connected to the clamp base 701;
c. an extender arm 704, such that a lower end of the extender arm is pivotally connected to the clamp base 701, such that an elevation angle can be adjusted; and
d. two adjustable side arms 706, which are pivotally connected to an upper end of the extender arm 704, such that the adjustable side arms 706 are in an opposing configuration;
such that the breast shield clamp 700 is connected to the mesh tray 102 with the clip 702, and the extender arm 704 can be adjusted by adjusting an elevation angle 710, and side arms 706 can be adjusted, by opening or narrowing a gap 720 between the side arms 706, to secure the breast flange connector 610, whereby the breast shield clamp 700 can be used to secure a breast flange connector 610 in place.

As shown in FIG. 7, some breast flange designs may be cleaned better when a broad part of the flange is facing down, and the clamp can be used for stabilization of the flange. The clamp 700 can further include a first pivotal point 742, which pivotally connects the clamp base 701 and the extender arm 704. The clamp 700 can further include a second pivotal point 744, which pivotally connects the extender arm 704 with the side arms 706. The first and second pivotal points 742 744 can include spring tension and movement in click steps.

Figure 8:
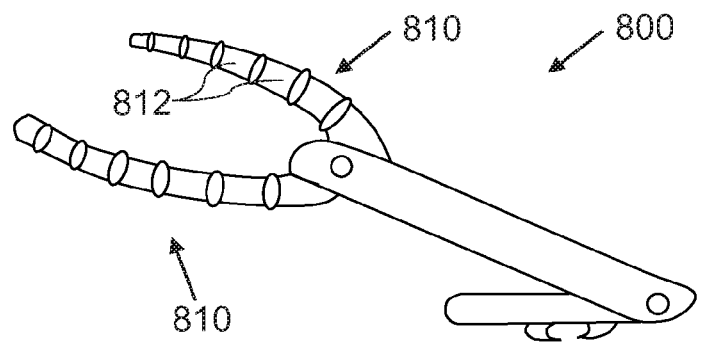
FIG. 8 is a perspective view of a breast shield clamp with flexible side arms, according to an embodiment of the invention.

In a related embodiment, as shown in FIG. 8, a breast shield clamp 800 can have flexible side arms 810, for example of the goose neck type, comprising pivotally connected segments 812, such that the shape of the side arms 810 can be adjusted.

In a further related embodiment, as shown in FIG. 2, the washer 100 can include a steam generator 250 to generate steam and thereby sterilize the contents. The steam generator 250 can be attached inside the washer enclosure, mounted to a sidewall above the tray, and connected to the tube network 558. The steam generator 250, can be manufactured in a configuration similar to small boilers used to generate steam in espresso machines, such as for example an espresso boiler model number CTC-31, manufactured by Succway™.

In a further related embodiment, the washer 100 can include an ultraviolet sterilizer lamp 260 configured to emit sterilizing light onto items mounted in the tray 102, and thereby sterilize the items. The ultraviolet sterilizer lamp 260 can be located inside the washer enclosure, mounted to a sidewall above the tray.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:
1. A washing device for washing breast pump accessories, comprising:
a. a washing enclosure, comprising side walls, a base section, and a hinged front door;

b. a water inlet;
c. a drain outlet;
d. a tube network, wherein the tube network is mounted in the washing enclosure, and is configured in fluid connection with the water inlet and the drain outlet;
e. a wash pump, which is mounted inside the washing enclosure, wherein the wash pump is configured to pump water in the tube network, such that the water circulates in the tube network;
f. a heating element, which is connected to the tube network, such that the heating element heats the water in the tube network;
g. a tray;
h. a plurality of water dispensing components, comprising:
a plurality of spray pipes, wherein each spray pipe comprises a spray nozzle which is connected to the tube network, wherein each spray pipe is connected to the tray; and
i. at least one breast shield clamp, comprising:
an extender arm, such that a lower end of the extender arm is pivotally connected to the tray, configured such that an elevation angle is adjustable; and
two adjustable side arms, which are pivotally connected to an upper end of the extender arm, such that the adjustable side arms are in an opposing configuration, such that the adjustable side arms are adjusted, by opening or narrowing a gap between the side arms;
such that the adjustable side arms each are configured with an open end that is distal to a connected end, which is connected to the upper end of the extender arm, such that the open ends of the adjustable side arms are configured to reach around opposing sides of a breast flange of a breast flange connector, when a broad part of the breast flange is facing down;
whereby the at least one breast shield clamp is used to secure the breast flange connector in place.

2. The washing device of claim 1, further comprising a distribution valve, which is connected to the tube network, such that the distribution valve is configured to selectively pump the water to a selected set of components, selected from the water dispensing components.

3. The washing device of claim 1, wherein at least one of the spray pipes comprises a spray nozzle that is a rotating spray nozzle.

4. The washing device of claim 1, wherein at least one of the spray pipes comprises a spray nozzle that is a flexible elongated spray nozzle, configured such that the shape of the flexible elongated spray nozzle is adjustable.

5. The washing device of claim 4, wherein the flexible elongated spray nozzle further comprises pivotally connected segments.

6. The washing device of claim 1, wherein at least one of the spray pipes is configured as a height adjustable spray pipe, such that the height of the spray pipe is adjustable.

7. The washing device of claim 6, wherein the height adjustable spray pipe further comprises an upper pipe and a lower pipe, such the upper pipe is configured to slide inside the lower pipe, when the height of the height adjustable spray pipe is adjusted.

8. The washing device of claim 1, further comprising a bottom spinner, which is rotationally mounted at a bottom inner side of the washing device, such that the bottom spinner is connected to the tube network, wherein the bottom spinner comprises a plurality of blades, wherein each blade comprises a plurality of holes, which allow jets of the water to be sprayed on contents in the tray from the bottom, wherein the holes are angled such that the jets cause the bottom spinner to spin.

9. The washing device of claim 1, further comprising an upper spinner, which is rotationally mounted at an upper inner side of the washing device, such that the upper spinner is connected to the tube network, wherein the upper spinner comprises a plurality of blades, wherein each blade comprises a plurality of holes, which allow jets of the water to be sprayed on contents in the tray from the top, wherein the holes are angled such that the jets cause the upper spinner to spin.

10. The washing device of claim 1, further comprising at least one side spinner, which is mounted on at least one inner side of the washing enclosure, such that the at least one side spinner is connected to the tube network, wherein the at least one side spinner comprises a plurality of blades, wherein each blade comprises a plurality of holes, which allow jets of the water to be sprayed on contents in the tray from the inner side, wherein the holes are angled such that the jets cause the at least one side spinner to spin.

11. The washing device of claim 1, further comprising at least one side nozzle, which is mounted on at least one inner side of the washing enclosure, such that the at least one side nozzle is connected to the tube network, wherein the at least one side nozzle is configured to spray the water on the contents of the tray.

12. The washing device of claim 11, wherein the at least one side nozzle is a rotating side nozzle.

13. The washing device of claim 11, wherein the at least one side nozzle is an adjustable side nozzle, configured such that the adjustable side nozzle is manually adjustable to spray in a pre-determined direction.

14. The washing device of claim 1, further comprising grooves on the side walls of the washing enclosure and a top sliding mesh lid, such that the top sliding mesh lid slides into the grooves, whereby the top sliding mesh lid supports bottles and breast flange connectors that are positioned below in the tray.

15. The washing device of claim 1, wherein the adjustable side arms, are configured as flexible side arms, such that shapes of each of the side arms are adjustable.

16. The washing device of claim 15, wherein the adjustable side arms comprise pivotally connected segments.

17. The washing device of claim 1, further comprising a steam generator, wherein the steam generator is attached inside the washing enclosure, and connected to the tube network, whereby the steam generator generates steam and thereby sterilizes contents in the tray.

18. The washing device of claim 1, further comprising at least one ultraviolet sterilizer lamp, wherein the ultraviolet sterilizer lamp is attached inside the washing enclosure, such that the ultraviolet sterilizer lamp is configured to emit sterilizing light onto items mounted in the tray, whereby the ultraviolet sterilizer lamp sterilizes the items.

* * * * *